United States Patent
Lee et al.

(10) Patent No.: US 7,528,265 B2
(45) Date of Patent: May 5, 2009

(54) PROCESS FOR THE PREPARATION OF SIMVASTATIN

(75) Inventors: Jaeheon Lee, Yongin-si (KR); Taehee Ha, Suwon-si (KR); Chulhyun Park, Seongnam-si (KR); Hoechul Lee, Yongin-si (KR); Gwansun Lee, Seoul (KR); Youngkil Chang, Seoul (KR)

(73) Assignee: Hanmi Pharm., Co., Ltd. (KR)

( * ) Notice: Subject to any disclaimer, the term of this patent is extended or adjusted under 35 U.S.C. 154(b) by 751 days.

(21) Appl. No.: 10/501,007

(22) PCT Filed: Dec. 26, 2002

(86) PCT No.: PCT/KR02/02434

§ 371 (c)(1),
(2), (4) Date: Jul. 8, 2004

(87) PCT Pub. No.: WO03/057684

PCT Pub. Date: Jul. 17, 2003

(65) Prior Publication Data

US 2005/0080275 A1    Apr. 14, 2005

(30) Foreign Application Priority Data

Jan. 9, 2002    (KR) .................. 10-2002-0001118

(51) Int. Cl.
*C07D 309/30* (2006.01)

(52) U.S. Cl. .................................... 549/292

(58) Field of Classification Search .................. 549/292
See application file for complete search history.

(56) References Cited

U.S. PATENT DOCUMENTS

| 4,444,784 A | * | 4/1984 | Hoffman et al. | ............ 514/460 |
| 5,159,104 A | * | 10/1992 | Dabora et al. | ............... 560/119 |
| 6,331,641 B1 | * | 12/2001 | Taoka et al. | ................. 549/292 |

FOREIGN PATENT DOCUMENTS

| WO | WO 01/00606 A1 | 1/2001 |
| WO | WO 01/30773 A2 | 5/2001 |
| WO | WO 01/45484 A2 | 6/2001 |

OTHER PUBLICATIONS

No Author, "Dean-Stark apparatus" [online]. Wikipedia 2006. Retreived from the Internet < http://www.answers.com/main/ntquery?s=Dean%2DStark%20apparatus&print=true>.*

* cited by examiner

*Primary Examiner*—Janet L. Andres
*Assistant Examiner*—Raymond Covington
(74) *Attorney, Agent, or Firm*—Sughrue Mion, PLLC

(57) ABSTRACT

Highly pure simvastatin can be prepared economically in a high yield using the method comprising the steps of treating lovastatin with potassium hydroxide dissolved in a mixture of water and methanol to obtain a triol acid; relactonizing the triol acid, and protecting the hydroxy group on the lactone ring; and acylating the resulting compound with 2,2-dimethylbutyryl chloride or 2,2-dimethylbutyryl bromide in the presence of an acylation catalyst in an organic solvent, followed by removing the silyl protecting group on the lactone ring to obtain simvastatin.

8 Claims, No Drawings

PROCESS FOR THE PREPARATION OF SIMVASTATIN

FIELD OF THE INVENTION

The present invention relates to a low-cost process for preparing high-purity simvastatin in a high yield.

BACKGROUND OF THE INVENTION

Some hexahydronaphthalene derivatives, e.g., lovastatin, atorvastatin, cerivastatin and simvastatin, are potent inhibitors of HMG-CoA(3-hydroxy-3-methylglutaryl CoA) reductase, the enzyme which controls the biosynthesis of cholesterol, and therefore, used widely for the treatment of hyperlipidemia, hypercholesterolemia, and others. In particular, simvastatin of formula (1) is favored over other hexahydronaphthalene derivatives because of the absence of adverse side effects and its high absorbability in the stomach. Also, it has been reported that simvastatin prevents and reduces the risk of Alzheimer's disease(AD) by retarding the production of Ab42, β-amyloid protein related to the outbreak of AD.

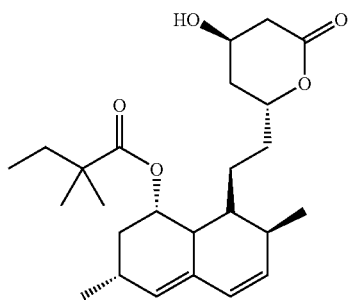

(I)

The synthesis of simvastatin from lovastatin have been conducted based mainly on one of the two following methods.

U.S. Pat. No. 5,393,893, U.S. Pat. No. 4,582,915, U.S. Pat. No. 5,763,646, U.S. Pat. No. 5,763,653, EP Patent No. 299,656 and International Patent Publication No. WO 99/45003 disclose a method of preparing simvastatin of formula (I) by way of direct methylation of the 8'-methylbutyryloxy side chain of lovastatin of formula (II) using a methyl halide in the presence of a metal amide base. However, this method has the disadvantage that the C-methylation step has to be carried out at an extremely low temperatures(−75 to −30° C.) using a strong base under anhydrous condition which is difficult to handle in mass production.

Another method disclosed in U.S. Pat. No. 4,444,784 is represented by Scheme 1. First, lovastatin of formula (II) is hydrolyzed with an excessive amount of lithium hydroxide to remove the 2-methylbutyryl side chain and to simultaneously open its 6-membered lactone ring to produce the triol acid of formula (III). The triol acid compound of formula (III) is then heated to obtain the diol lactone of formula (IV). The hydroxy group on the lactone ring of the diol lactone is protected to obtain the tert-butyldimethylsilyl ether of formula (V) and then the hydroxy group at C-8 of the hexahydronaphthalene ring system is acylated with 2,2-dimethylbutaonic acid in the presence of dicyclohexyl carbodiimide, or 2,2-dimethyl chloride to produce the compound of formula (VI). The t-butyldimethylsilyl protecting group of the compound of formula (VI) is then removed in the final step using tetrabutylammonium fluoride to produce simvastatin of formula (I):

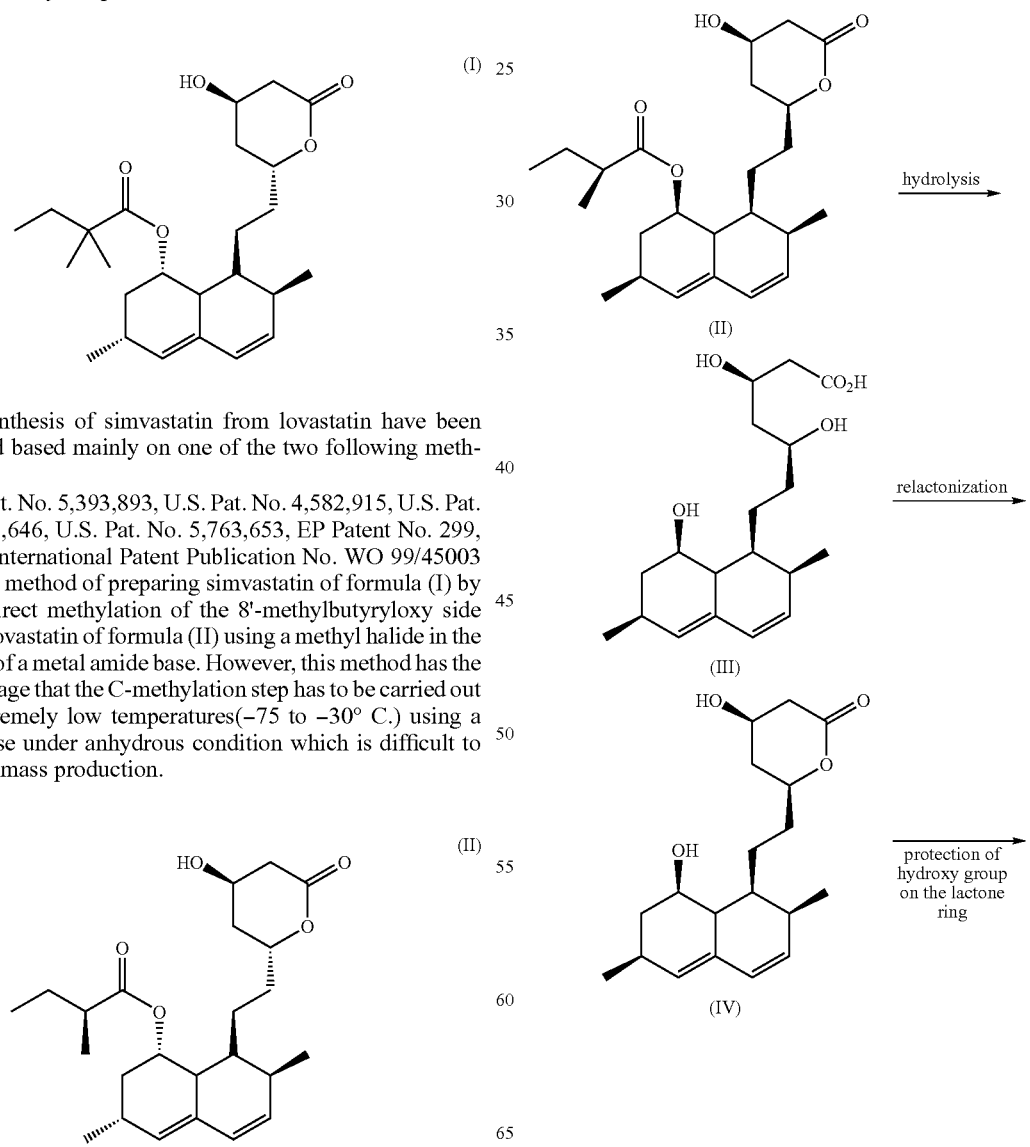

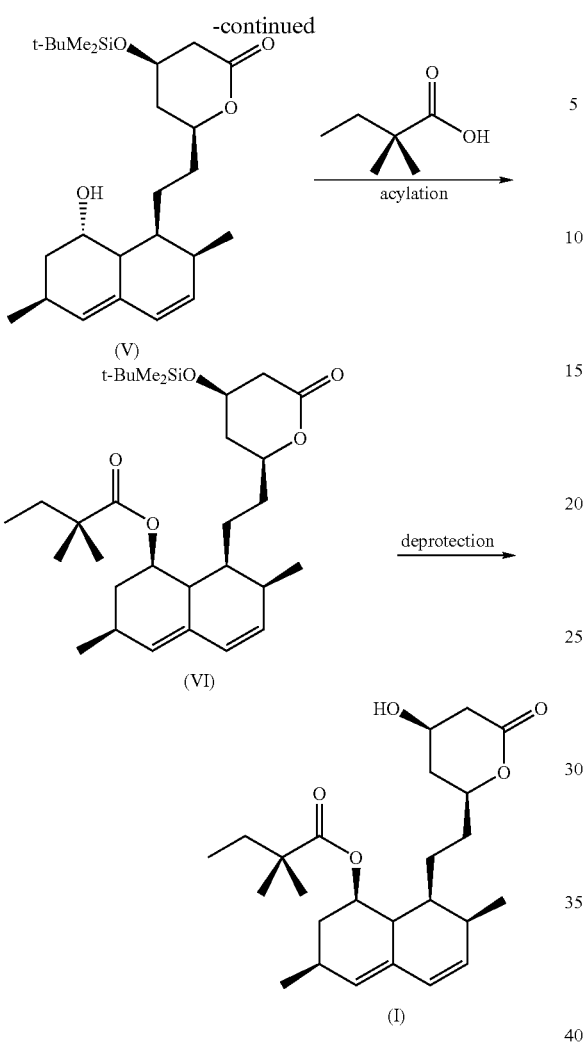

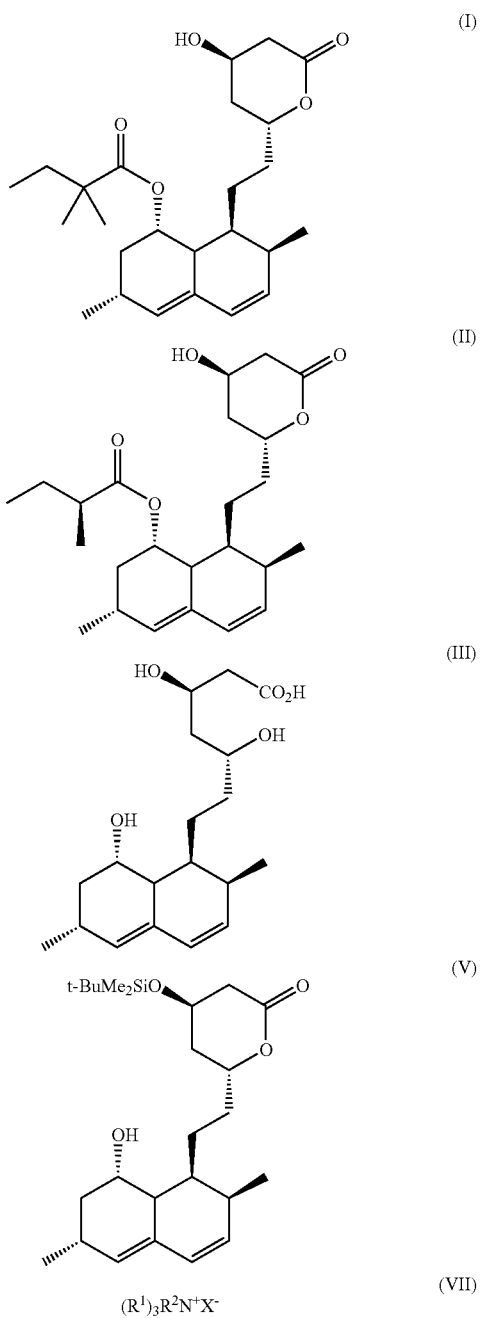

However, this method requires a high temperature and 56 hours of long reaction time in the hydrolysis and acylation steps, which leads to a number of undesired side products, causing low yield and purity of the final product.

In addition, Korean Publication No. 2000-15179 discloses a modification of the method of reaction scheme 1, wherein t-BuOK is used in the hydrolysis step, and acyloxy triphenylphosphonium salts, in the acylation step. However, this method requires the use of t-BuOK which is expensive and causes unwanted side reaction and gives low yield, and excessively large amounts of reagents such as 2,2-dimethyl butanoic acid, triphenyl phosphine and N-bromosuccinimide, the unreacted reagents being removed by complicated purification procedures. Thus, like the other methods, this method is also not suitable for mass production.

SUMMARY OF THE INVENTION

Accordingly, it is a primary object of the present invention to provide an improved process for preparing simvastatin of high-purity in a high yield, which can be advantageously used for mass production of simvastatin.

In accordance with one aspect of the present invention, there is provided a method of preparing simvastatin of formula (I) comprising the steps of:

(a) treating lovastatin of formula (II) with potassium hydroxide dissolved in a mixture of water and methanol to obtain the compound of formula (III);

(b) relactonizing the compound of formula (III), and protecting the hydroxy group on the lactone ring to obtain the compound of formula (V); and (c) acylating the compound of formula (V) with 2,2-dimethylbutyryl chloride or 2,2-dimethylbutyryl bromide in the presence of an acylation catalyst which is a compound of formula (VII) or a compound of formula (VIII) in an organic solvent, followed by removing the silyl protecting group on the lactone ring to obtain simvastatin of formula (I).

-continued $$(R^1)_3R^2P^+X^- \quad (VIII)$$

wherein $R^1$ is $C_{1-20}$ alkyl or phenyl; $R^2$ is $C_{1-20}$ alkyl, phenyl, or benzyl; and X is Br or I.

DETAILED DESCRIPTION OF THE INVENTION

The method of the present invention makes it possible to prepare highly pure simvastatin in a high yield under a mild condition, by using potassium hydroxide dissolved in a mixture of water and methanol in the hydrolysis step (a), and an acylation catalyst such as quaternary ammonium halides and quaternary phosphonium halides in the acylation step (c).

The method of the present invention is described in detail as follows:

Step (a)

Potassium hydroxide is employed in an amount ranging from 5 to 15 equivalents, preferably from 8 to 12 equivalents, based on the amount of lovastatin of formula (II).

Water and methanol may be used in a ratio(v:v) of 1:2 to 1:20, preferably 1:4 to 1:12, and the water and methanol mixture may be used in an amount of 1 to 8 ml, preferably 4 to 6 ml, per 1 g of potassium hydroxide.

The hydrolysis step may be performed at a temperature ranging from 20 to 80° C., preferably from 50 to 70° C., for about 5 to 12 hours, to give the compound of formula (III) as a white solid having a purity of at least 98%, in a high yield of at least 95%, 10% higher than that of the 56 hours long hydrolysis step with t-BuOK of the conventional method.

Step (b)

This step may be performed modifying the conventional method(U.S. Pat. No. 4,444,784) to give the compound of formula (V) having a purity of at least 98% in a yield of 90% or higher.

Step (c)

In this process, the compound of formula (V) prepared in step (b) may be refluxed together with 2,2-dimethylbutyryl halide in the presence of an acylation catalyst such as a quaternary ammonium halide or a quaternary phosphonium halide in benzene while azeotropically removing water using a Dean-stark trap, to give a compound of formula (VI) having a purity of at least 98% in a yield of 95% or higher. The acylation catalyst facilitates the completion of the reaction within 6 to 8 hours, which should be compared with 3 to 4 days required in the conventional method.

The quaternary ammonium halide compound which may be used in the present invention includes benzyltri-n-butylammonium bromide, benzyltriethylammonium bromide, n-decyltrimethylammonium bromide, n-dodecyltrimethylammonium bromide, n-octyltrimethylammonium bromide, phenyltrimethylammonium bromide, tetra-n-butylammonium bromide, tetraethylammonium bromide, tetra-n-hexylammonium bromide, tetramethylammonium bromide, tetra-n-propylammonium bromide, benzyltriethylammonium iodide, phenyltriethylammonium iodide, phenyltrimethylammonium iodide, tetra-n-butylammonium iodide, tetra-n-heptylammonium iodide, tetra-n-hexylammonium iodide, tetra-n-octylammonium iodide, tetra-n-propylammonium iodide and tetramethylammonium iodide, etc., among which benzyltri-n-butylammonium bromide and tetra-n-butylammonium bromide are most preferred.

Further, the quaternary phosphonium halide compound which may be used in the present invention includes benzyltriphenylphosphonium bromide, n-butyltriphenylphosphonium bromide, methyltriphenylphosphonium bromide, ethyltripheny phosphonium bromide, n-heptyltriphenylphosphonium bromide, n-hexyltriphenylphosphonium bromide, n-propyltriphenylphosphonium bromide, tetra-n-butylphosphonium bromide, tetra-n-octylphosphonium bromide, tetraphenylphosphonium bromide, tetraphenylphosphonium iodide and methyltriphenylphosphonium iodide, etc., among which tetra-n-butylphosphonium bromide is most preferred.

The quaternary ammonium halide or quaternary phosphonium halide may be used in an amount ranging from 0.5 to 3.0 equivalents, preferably from 0.8 to 1.5 equivalents, based on the amount of the compound of formula (V).

2,2-dimethylbutyryl chloride or 2,2-dimethylbutyryl bromide may be used in an amount ranging from 1 to 3 equivalents, preferably from 1.3 to 1.8 equivalents, based on the amount of the compound of formula (V).

Also, pyridine may be added to the above reaction mixture to neutralize HCl produced in an amount ranging from 2 to 4 equivalents, based on the amount of the compound of formula (V).

Subsequently, the removal of the t-butyldimethylsilyl protecting group of the compound (VI) may be carried out by the conventional method(U.S. Pat. No. 4,444,784) to obtain simvastatin of formula (I) having a purity of at least 99% in a high yield of 90% or higher.

As described above, according to the present invention, highly pure simvastatin can be obtained in a high yield at a low production cost.

The following Examples are given for the purpose of illustration only, and are not intended to limit the scope of the invention.

EXAMPLE

Example 1

Preparation of 7-[1',2',6',7',8',8a'(R)-hexahydro-2'(S), 6'(R)-dimethyl-8'(S)-hydroxy-1'(S)-naphthyl]-3(R),5 (R)-dihydroxy heptanoic acid (the compound of formula (III))

140 g of potassium hydroxide was dissolved in 100 ml of water, and 600 ml of methanol was added slowly thereto while keeping the temperature at 20° C. using an ice bath, followed by adding 100 g of lovastatin thereto at 20° C. The mixture was refluxed using an oil bath for 8 hours, and 150 ml of water was added thereto. Subsequently, methanol was removed under a reduced pressure, and 550 ml of water and 300 ml of diethylether were added thereto. The mixture was acidified by slowly adding 6N—HCl at 5 to 10° C. with stirring, and stirred for additional 30 minutes at the same temperature. The resulting precipitates were filtered, washed with a mixture of water and diethylether, and dried, to obtain 82 g of the title compound as a white solid(yield: 98%, purity: 98.6%).

m.p.: 128° C.

$^1$H-NMR($\delta$, CDCl$_3$): 5.98(d, 1H), 5.80(dd, 1H), 5.54(bs, 1H), 4.33(m, 1H), 4.28(m, 1H), 3.98(m, 1H), 2.51(bs, 2H), 1.18(d, 3H), 0.90(d, 3H)

Example 2

Preparation of 6(R)-[2-(8'(S)-hydroxy-2'(S),6'(R)-dimethyl-1',2',6',7',8',8a'(R)-hexahydronaphthyl-1'(S))ethyl]-4(R)-hydroxy-3,4,5,6-tetrahydro-2H-pyran-2-one(the compound of formula (IV))

79 g of 7-[1',2',6',7',8',8a'(R)-hexahydro-2'(S),6'(R)-dimethyl-8'(S)-hydroxy-1'(S)-naphthyl]-3(R),5(R)-dihydroxy heptanoic acid prepared in Example 1 was dissolved in 560 ml of ethyl acetate, and 0.8 g of p-toluene sulfonic acid was added thereto. The reaction mixture was stirred at room temperature for 3 hours, followed by addition of 700 ml of hexane, and stirred for additional 30 minutes. The resulting precipitates were then filtered, washed with 100 ml of hexane, and dried, to obtain 73.5 g of the title compound as a white solid(yield: 98%, purity: 98.2%).

m.p.: 125-126° C.

$^1$H-NMR($\delta$, CDCl$_3$): 6.0(d, 1H), 5.80(dd, 1H), 5.54(bs, 1H), 4.72(m, 1H), 4.38(m, 1H), 4.23(bs, 1H), 2.68(dd, 2H), 2.39(m, 2H), 2.15-1.78(m, 9H), 1.58-1.18(m, 4H), 1.19(d, 3H), 0.90(m, 1H)

Example 3

Preparation of 6(R)-[2-(8'(S)-hydroxy-2'(S),6'(R)-dimethyl-1',2',6',7',8',8a'(R)-hexahydronaphthyl-1'(S))ethyl]4(R)-(dimethyl-tert-butyl silyloxy)-3,4,5,6-tetrahydro-2H-pyran-2-one (the compound of formula (V))

70 g of 6(R)-[2-(8'(S)-hydroxy-2'(S),6'(R)-dimethyl-1',2',6',7',8',8a' (R)-hexahydronaphthyl-1'(S))ethyl]4(R)-hydroxy-3,4,5,6-tetrahydro-2H-pyran-2-one prepared in Example 2 was dissolved in 800 ml of dichloromethane, and 43 g of imidazole and 43 g of t-butyl dimethylchlorosilane were successively added thereto. The reaction mixture was stirred at 25 to 30° C. for 6 hours, and washed successively three times with 300 ml of water, 200 ml of 0.2 N—HCl, 100 ml of saturated sodium bicarbonate and 100 ml of saturated saline. The organic layer was then separated, dried over anhydrous MgSO$_4$, filtered and the solvent was removed. 300 ml of hexane was added to the resulting solid, and stirred at room temperature for 30 minutes. The resulting precipitates were filtered, and dried, to obtain 87.6 g of the title compound as a white solid(yield: 96%, purity: 98.5%).

m.p.: 134-136° C.

$^1$H-NMR($\delta$, CDCl$_3$): 6.03(d, 1H), 5.78(dd, 1H), 5.57(m, 1H), 4.70(m, 1H), 4.28(m, 2H), 2.58(d, 2H), 1.19(d, 3H), 0.90(s, 9H), 0.89(d, 3H). 0.1(s, 6H)

Example 4

Preparation of 6(R)-[2-(8'(S)-2'',2''-dimethylbutyryloxy-2'(S),6'(R)-dimethyl-1',2', 6',7',8',8a'(R)-hexahydronaphthyl-1'(S))ethyl]-4(R)-(dimethyl-tert-butylsilyloxy)-3,4,5,6-tetrahydro-2H-pyran-2-one (the compound of formula (VI))

10 g of benzyltri-n-butylammonium bromide and 2.3 ml of pyridine were added to 100 ml of benzene. The mixture was refluxed for 30 minutes using a Dean-stark trap, followed by addition of 5.2 ml of 2,2-dimethylbutyryl chloride and 10 g of 6(R)-[2-(8'(S)-hydroxy-2'(S),6'(R)-dimethyl-1',2',6',7',8',8a' (R)-hexahydronaphthyl-1'(S))ethyl]-4(R)-(dimethyl-tert-butylsilyloxy)-3,4,5,6-tetrahydro-2H-pyran-2-one prepared in Example 3, refluxed for additional 8 hours, and then cooled.

The resulting mixture was diluted with 300 ml of diethyl ether, and washed successively twice with 300 ml of water, 100 ml of 0.2N—HCl and 200 ml of saturated sodium bicarbonate. The organic layer was then separated, dried over anhydrous MgSO$_4$ and filtered. Evaporation of the solvent gave 12.1 g of the title compound as an oil(yield: 98%, purity: 98.3%).

$^1$H-NMR($\delta$, CDCl$_3$): 6.01(d, 1H), 5.80(dd, 1H), 5.52(bs, 1H), 5.35(bs, 1H), 4.60(m, 1H), 4.30(t, 2H), 2.60(m, 2H), 2.38(m, 2H), 2.20(d, 1H). 1.98-1.25(m, 14H), 1.12(d, 3H), 1.10(d, 3H), 0.95-0.81(m, 15H), 0.1(s, 6H)

Example 5

Preparation of 6(R)-[2-(8'(S)-2''0.2''-dimethylbutyryloxy-2'(S),6'(R)-dimethyl-1',2',6',7',8',8a'(R)-hexahydronaphthyl-1'(S))ethyl]-4(R)-hydroxy-3,4,5,6-tetrahydro-2H-pyran-2-one(the compound of formula (I))

12.3 g of 6(R)-[2-(8'(S)-2'',2''-dimethylbutyryloxy-2'(S),6'(R)-dimethyl-1',2',6',7',8',8a'(R)-hexahydronaphthyl-1'(S))ethyl]-4(R)-(dimethyl-tert-butyl silyloxy)-3,4,5,6-tetrahydro-2H-pyran-2-one prepared in Example 4 was dissolved in 100 ml of tetrahydrofuran, and 5 ml of acetic acid and 63 ml of 1N-tetrabutyl ammonium fluoride were successively added thereto. The mixture was stirred at room temperature for 48 hours, diluted with 800 ml of diethylether, and washed successively twice with 150 ml of water, 150 ml of 0.2N—HCl, 150 ml of water, 150 ml of saturated sodium bicarbonate and 150 ml of saturated saline. The organic layer was then separated, dried over anhydrous MgSO$_4$ and filtered. Evaporation of the solvent gave a crude product, which was recrystallized from ethyl acetate/hexane to obtain 8.8 g of the title compound as a white solid(yield: 91%, purity: 99.2%).

m.p.: 133-135° C.

$^1$H-NMR($\delta$, CDCl$_3$): 6.0(d, 1H), 5.78(dd, 1H), 5.51(bs, 1H), 5.37(m, 1H), 4.62(m, 1H), 4.39(bs, 1H), 2.92(m, 1H), 2.64-2.74(m, 2H), 2.4(m, 1H). 1.13(s, 6H), 0.86(t, 3H)

As shown above, the method of the present invention is capable of providing highly pure simvastatin in a high yield, at cost lower than the conventional methods.

While the invention has been described with respect to the specific embodiments, it should be recognized that various modifications and changes may be made by those skilled in the art to the invention which also fall within the scope of the invention as defined as the appended claims.

What is claimed is:

1. A method of preparing simvastatin of formula (I) comprising the steps of:
   (a) treating lovastatin of formula (II) with potassium hydroxide dissolved in a mixture of water and methanol to obtain the compound of formula (III);
   (b) relactonizing the compound of formula (III), and protecting the hydroxy group on the lactone ring to obtain the compound of formula (V); and
   (c) acylating the compound of formula (V) with 2,2-dimethylbutyryl chloride or 2,2-dimethylbutyryl bromide in the presence of an acylation catalyst which is a compound of formula (VII) or a compound of formula (VIII) in an organic solvent, followed by removing the silyl protecting group on the lactone ring to obtain simvastatin of formula (I):

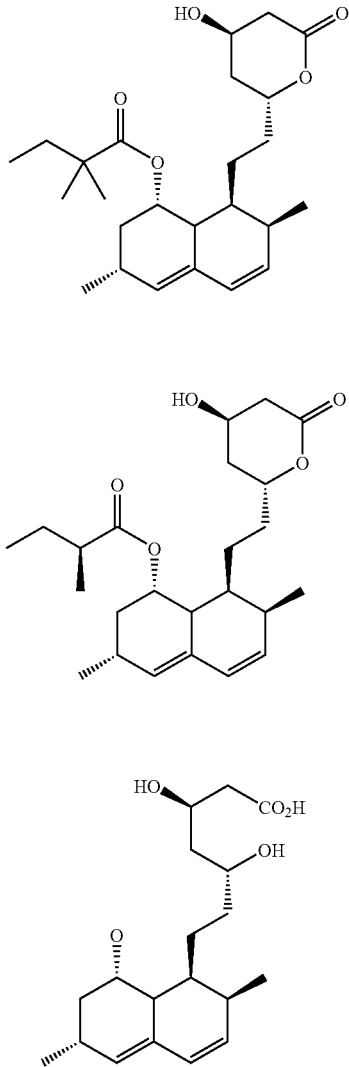

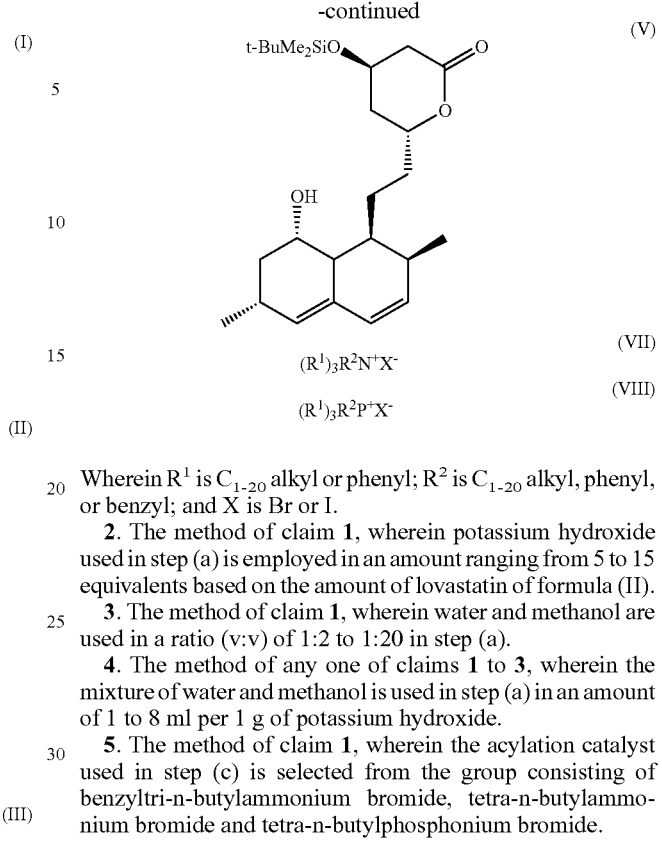

Wherein $R^1$ is $C_{1-20}$ alkyl or phenyl; $R^2$ is $C_{1-20}$ alkyl, phenyl, or benzyl; and X is Br or I.

2. The method of claim 1, wherein potassium hydroxide used in step (a) is employed in an amount ranging from 5 to 15 equivalents based on the amount of lovastatin of formula (II).

3. The method of claim 1, wherein water and methanol are used in a ratio (v:v) of 1:2 to 1:20 in step (a).

4. The method of any one of claims 1 to 3, wherein the mixture of water and methanol is used in step (a) in an amount of 1 to 8 ml per 1 g of potassium hydroxide.

5. The method of claim 1, wherein the acylation catalyst used in step (c) is selected from the group consisting of benzyltri-n-butylammonium bromide, tetra-n-butylammonium bromide and tetra-n-butylphosphonium bromide.

6. The method of claim 1 or 5, wherein the acylation catalyst used in step (c) is employed in an amount ranging from 0.5 to 3 equivalents based on the amount of the compound of formula (V).

7. The method of claim 1, wherein 2,2-dimethylbutyryl chloride or bromide used in step (c) is employed in an amount ranging from 1 to 3 equivalents based on the amount of the compound of formula (V).

8. The method of claim 1, wherein the acylation step (c) is carried out in refluxing benzene while azotropically removing water using a Dean-stark trap.

* * * * *